US008223043B2

(12) United States Patent
Hwang et al.

(10) Patent No.: US 8,223,043 B2
(45) Date of Patent: Jul. 17, 2012

(54) METHOD AND APPARATUS FOR COMPRESSING NUCLEOTIDE SEQUENCE DATA

(75) Inventors: Bai-Kuang Hwang, Hsinchu (TW);
Jenn-Yeh Fann, Hsinchu County (TW);
Chung-Fan Chiou, Hsinchu County (TW)

(73) Assignee: Industrial Technology Research Institute, Hsinchu (TW)

( * ) Notice: Subject to any disclaimer, the term of this patent is extended or adjusted under 35 U.S.C. 154(b) by 26 days.

(21) Appl. No.: 12/977,457

(22) Filed: Dec. 23, 2010

(65) Prior Publication Data

US 2011/0163898 A1    Jul. 7, 2011

Related U.S. Application Data

(60) Provisional application No. 61/282,168, filed on Dec. 23, 2009, provisional application No. 61/330,552, filed on May 3, 2010.

(51) Int. Cl.
*H03M 7/30* (2006.01)

(52) U.S. Cl. .......................................... 341/87; 435/325

(58) Field of Classification Search ............... 341/87, 341/50; 435/325, 320.1, 468, 6, 69.1, 412, 435/419, 198, 191, 193, 252.35, 235.1; 424/1.49, 424/183.1, 199.1, 146.1
See application file for complete search history.

(56) References Cited

U.S. PATENT DOCUMENTS 7,141,419 B2 * 11/2006 Creech et al. ................. 435/325

FOREIGN PATENT DOCUMENTS

| CN | 101430742 A | 5/2009 |
| WO | WO 2004/074990 A2 | 9/2004 |
| WO | WO 2004/097369 A2 | 11/2004 |

OTHER PUBLICATIONS

Flicek et al., "Sense from sequence reads: methods for alignment and assembly", Nature Methods Supplement, vol. 6, No. 11s, Nov. 2009 (Published Online Oct. 15, 2009), pp. S6-S12.
Huo et al., "A Multiple Alignment Approach for DNA Sequences Based on the Maximum Weighted Path Algorithms", Journal of Software, vol. 18, No. 2, Feb. 2007, pp. 185-195.
Zerbino et al., "Velvet: Algorithms for de novo short read assembly using de Bruijn graphs", Genome Research, vol. 18, Mar. 18, 2008, pp. 821-829.
Zhang et al., "An Eulerian Path Approach to Global Multiple Alignment for DNA Sequences", Journal of Computational Biology, vol. 10, No. 6, 2003, pp. 803-819.

* cited by examiner

*Primary Examiner* — Joseph Lauture
(74) *Attorney, Agent, or Firm* — Birch, Stewart, Kolasch & Birch, LLP

(57) ABSTRACT

The invention provides a data compression method, comprising: (a) obtaining a first reading sequence and a second reading sequence from an identical source by a receiving unit; (b) comparing the first reading sequence with the second reading sequence according to a comparison condition to generate a sequence comparison result by the processor; (c) outputting a final template sequence according to the sequence comparison result by the processor; (d) comparing the final template sequence to each of the first and second reading sequences, to generate a respective difference between the final template sequence and each of the first and second reading sequences by the processor; and (e) compressing the first and second reading sequences according to the final template sequences and all generated differences between the final template sequence and the first and second reading sequences, to generate a compression file by the processor.

36 Claims, 12 Drawing Sheets

METHOD AND APPARATUS FOR COMPRESSING NUCLEOTIDE SEQUENCE DATA

CROSS REFERENCE TO RELATED APPLICATIONS

This application claims the benefit of U.S. Provisional Application No. 61/282,168, filed on Dec. 23, 2009, and U.S. Provisional Application No. 61/330,552, filed on May 3, 2010, the entirety of which is incorporated by reference herein.

BACKGROUND OF THE INVENTION

1. Field of the Invention

The invention relates to methods and apparatuses, and in particular relates to methods and apparatuses for compressing nucleotide sequence data.

2. Description of the Related Art

As the continuing development of single molecule DNA sequencing techniques, we can expect that enormous and growing amount of DNA read sequences are being generated. In order to achieve higher accuracy of DNA sequencing, sequencer generates dozens, maybe hundreds of raw sequences for each and all DNA segments.

According to a sequencing-by-synthesis DNA sequencer, DNA segments are synthesized in multiple copies by way of using a designed primer and polymerase. Then the fluorescent signals are received by the sensors, identified by the algorithm and output the result A, C, G, and T.

There are more than 3 billion DNA base pairs in a human genome. If raw read sequences generated by a sequencer in each genome sequencing process are more than ten times, even hundred times of a genome, as previously described, there will be an enormous amount of sequencing data. Intuitively, such huge amount of data definitely causes the burden in preserving, computation, as well as communication. We will have to downsize these data as the first thing in a high throughput processing system.

When running a DNA sequencing process, there are continuous DNA synthesis signals coming out from the detecting devices. These signals are being translated to DNA data in real-time devices. None of these signal or data can afford lost or missing in between. There is a need for efficient and convenient compression algorithm.

The path of the starting sequencing signals to raw sequences in storage includes three stages: (1) sequencing signals to raw data, (2) raw data to raw sequence in data storage, (3) raw sequence to sequence in computer storage and vice versa. Nowadays, personal computer communicates these data with its peripherals in a speed between 100 M bytes to some Giga bytes per second. The critical point in the path would be obviously in the interface between PC and its peripherals or devices.

BRIEF SUMMARY OF THE INVENTION

In one embodiment, the invention provides a data compression method, comprising: (a) obtaining a first reading sequence and a second reading sequence from an identical source by a receiving unit; (b) comparing the first reading sequence with the second reading sequence according to a comparison condition to generate a sequence comparison result by the processor; (c) outputting a final template sequence according to the sequence comparison result by the processor; (d) comparing the final template sequence to each of the first and second reading sequences, to generate a respective difference between the final template sequence and each of the first and second reading sequences by the processor; and (e) compressing the first and second reading sequences according to the final template sequences and all generated differences between the final template sequence and the first and second reading sequences, to generate a compression file by the processor, wherein the comparison condition is set according to a first seed table of the first reading sequence comprises a plurality of first seeds with a specific length constituting a plurality of first seed sets with different seeding start sites and a second seed table of the second reading sequence comprises a plurality of second seeds with a specific length constituting a plurality of second seed sets with different seeding start sites, and wherein the specific length of the first seeds of the first seed table and the specific length of the second seeds of the second seed table are of the same specific length.

In another embodiment, the invention provides a data compression method, comprising: (a) obtaining a plurality of reading sequences from an identical source by a receiving unit; (b) selecting one of the plurality of reading sequences as an initial template sequence by the processor; (c) comparing the initial template sequence to each of the other sequences according to a comparison condition, to respectively generate comparison results by the processor; (d) generating a sequence comparison result according to all respectively generated comparison results by the processor; (e) outputting a final template sequence according to the sequence comparison result by the processor; (f) comparing the final template sequence to each of the plurality of reading sequences, to generate a respective difference between the final template sequence and each of the plurality of reading sequences by the processor; and (g) compressing the plurality of reading sequences according to the final template sequences and all generated differences between the final template sequence and the plurality of reading sequences, to generate a compression file by the processor, wherein the comparison condition is set according to a first seed table of the initial template sequence comprises a plurality of first seeds with a specific length constituting a plurality of first seed sets with different seeding start sites and a second seed table of the reading sequence which is not selected comprises a plurality of second seeds with a specific length constituting a plurality of second seed sets with different seeding start sites, and wherein the specific length of the first seeds of the first seed table and the specific length of the second seeds of the second seed table are of the same specific length.

In one embodiment, the invention provides a sequence compression device, comprising: a receiving unit for obtaining a plurality of reading sequences from an identical source; and a processor for performing steps which comprise: (a) selecting one of the plurality of reading sequences as an initial template sequence; (b) comparing the initial template sequence to each of the other sequences according to a comparison condition, to respectively generate comparison results; (c) generating a sequence comparison result according to all respectively generated comparison results; (d) outputting a final template sequence according to the sequence comparison result; (e) comparing the final template sequence to each of the plurality of reading sequences, to generate a respective difference between the final template sequence and each of the plurality of reading sequences by the processor; and (f) compressing the plurality of reading sequences according to the final template sequences and all generated differences between the final template sequence and the plurality of reading sequences, to generate a compression file by the processor, wherein the comparison condition is set according to a first seed table of the initial template sequence comprises a plurality of first seeds with a specific length constituting a plurality of first seed sets with different seeding start sites and a second seed table of the reading sequence which is not selected comprises a plurality of second seeds with a specific length constituting a plurality of second seed sets with different seeding start sites, and wherein the specific length of the first seeds of the first seed table and the specific length of the second seeds of the second seed table are of the same specific length.

BRIEF DESCRIPTION OF THE DRAWINGS

The present invention can be more fully understood by reading the subsequent detailed description and examples with references made to the accompanying drawings, wherein:

FIG. 2b shows a simplified flow chart of one embodiment of step 205 of FIG. 2a;

FIG. 3b shows a simplified flow chart of one embodiment of step 307 of FIG. 3a.

FIG. 3c shows a simplified flow chart of one embodiment of step 309 of FIG. 3a.

DETAILED DESCRIPTION OF THE INVENTION

The following description is of the best-contemplated mode of carrying out the invention. This description is made for the purpose of illustrating the general principles of the invention and should not be taken in a limiting sense. The scope of the invention is best determined by reference to the appended claims.

The invention provides a sequence compression method and a device for performing the sequence compression method.

In the invention, the foundation of the sequence compression method is to compare two sequences.

The sequence compression method is detailed in the following, in one aspect of the invention.

Figure 1:
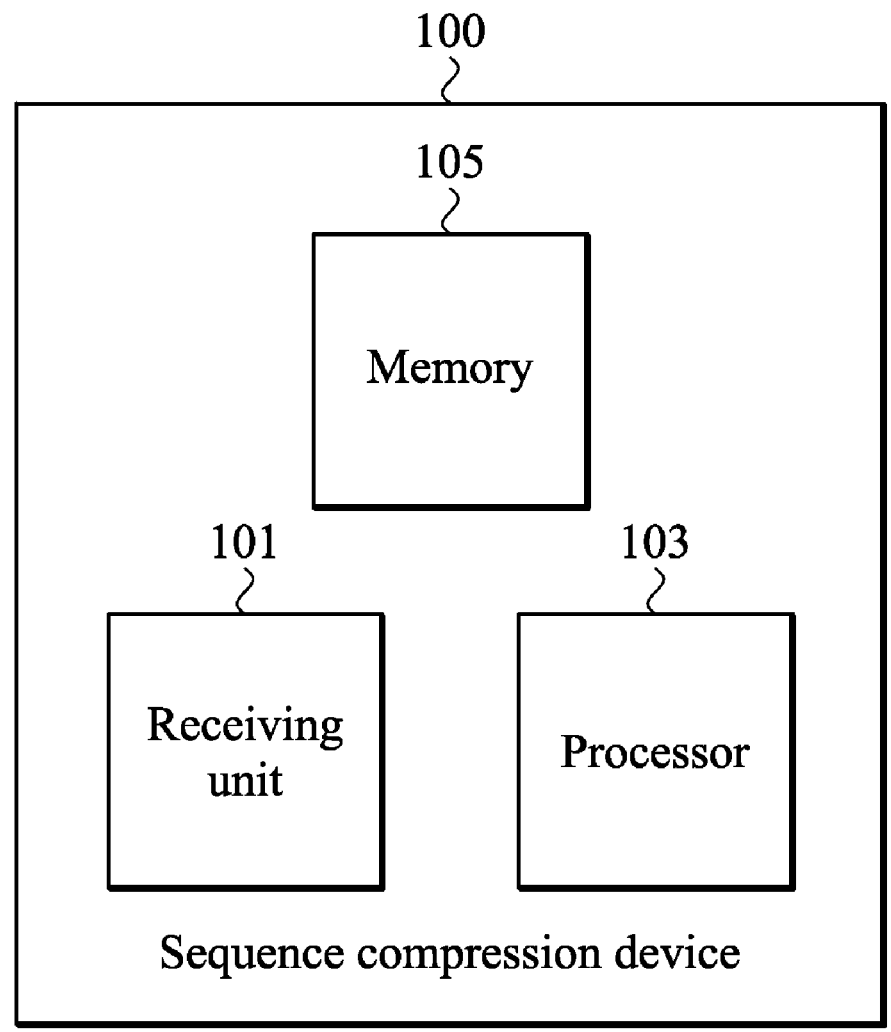
FIG. 1 shows a diagram of one embodiment of a sequence compression device of the invention.
Figure 2A:
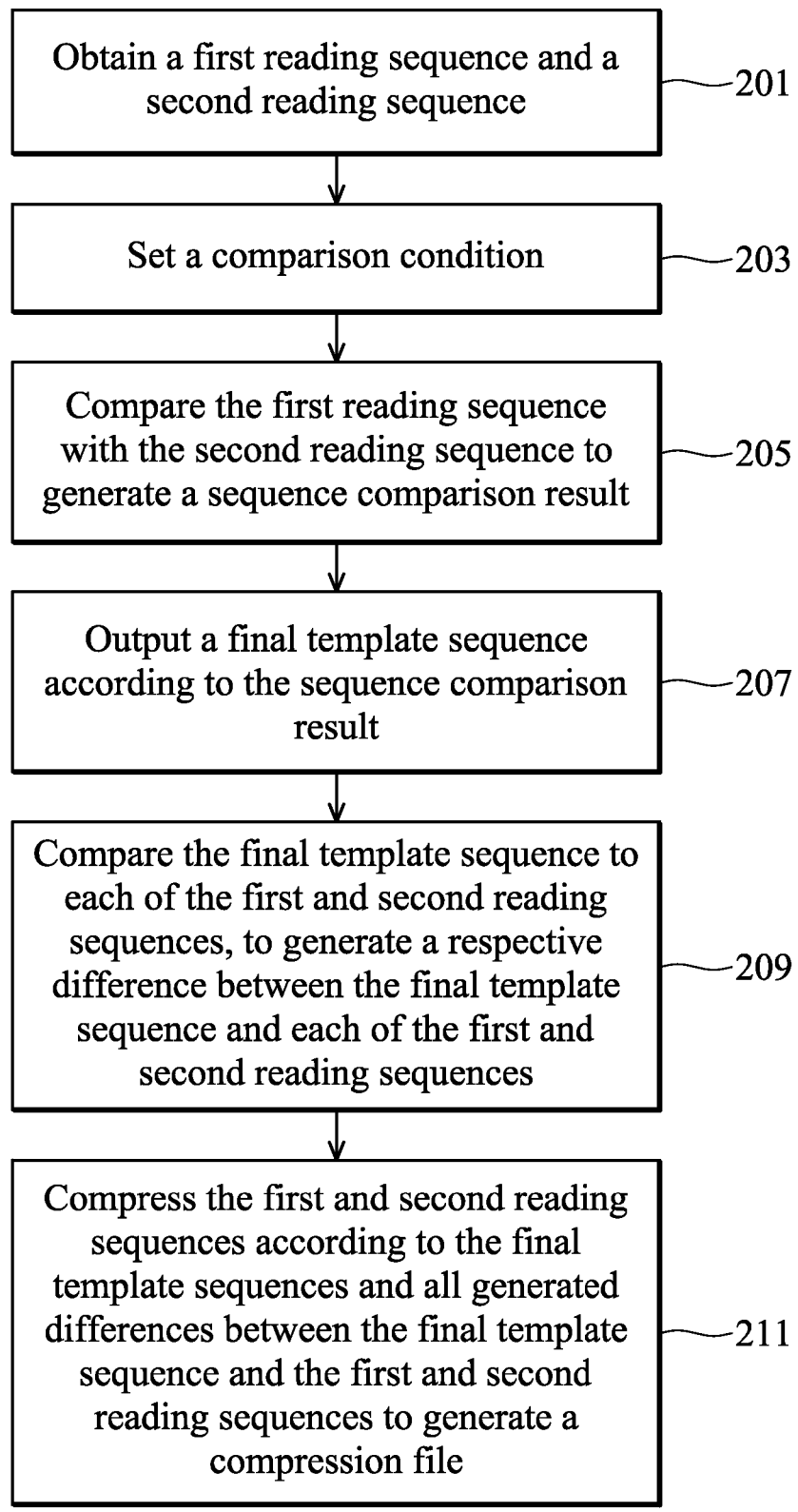
FIG. 2a shows a simplified flow chart of one embodiment of a sequence compression method for two reading sequences.

Referring to FIG. 1 and FIG. 2a, FIG. 1 shows a diagram of one embodiment of a sequence compression device of the invention and FIG. 2a shows a simplified flow chart of one embodiment of the sequence compression method performed by the device. The sequence compression device 100 may comprises a receiving unit 101, a processor 103, and a memory 105. First, the receiving unit 101 obtains a first reading sequence and a second reading sequence from an identical source (step 201). Next, the processor 103 sets a comparison condition (step 203). After the comparison condition is set, the processor 103 compares the first reading sequence with the second reading sequence according to the comparison condition to generate a sequence comparison result (step 205). Then, the processor 103 outputs a final template sequence according to the sequence comparison result (step 207). In another embodiment, the final template sequence may be selected from the first reading sequence or the second reading sequence. The final template sequence may be stored in the memory 105. After then, the processor 103 compares the final template sequence to each of the first and second reading sequences in order to generate a respective difference between the final template sequence and each of the first and second reading sequences (step 209). The respective difference may include starting positions, lengths, ending positions, and contents. Finally, the processor 103 compresses the first and second reading sequences according to the final template sequences and all generated differences between the final template sequence and the first and second reading sequences in order to generate a compression file (step 211). The compression file may have a file format comprising a file header, the final template sequence, and a comparison difference of positions and contents corresponding to all generated differences between the final template sequence and the first and second reading sequences.

The processor 103 may set the comparison condition according to a first seed table of the first reading sequence and a second seed table of the second reading sequence. The first seed table of the first reading sequence may comprise a plurality of first seeds with a specific length constituting a plurality of first seed sets with different seeding start sites and the second seed table of the second reading sequence may comprise a plurality of second seeds with a specific length constituting a plurality of second seed sets with different seeding start sites, wherein the specific length of the first seeds of the first seed table and the specific length of the second seeds of the second seed table are of the same specific length.

A seed table of a sequence may be built by the processor 103, wherein a seed is a segment of the sequence. An example of building a seed table of a sequence is detailed in the following.

A sequence is divided into a plurality of seeds (or segment) sets from the different start sites of the sequence, respectively, by per seed (or segment) K mers (a specific length of the seeds), wherein K is a positive integer of greater than 2, preferably 2-9, more preferably 3-9 and a content and a position of each seed are recorded, and then a seed table of the sequence is built. The basis for choosing the specific length of the seeds for dividing the sequence may comprise experiences of a user, the length of the sequence or the accuracy of a prior final template sequence from the calibration method of the invention, but not limited thereto, wherein the accuracy of a prior final template sequence may be obtained by comparing a know sequence of a know primer with the final template sequence thereof obtained from the calibration method of the invention. In one embodiment, the specific length per seed may be chosen according to experiences of a user. In another embodiment, the specific length per seed is chosen according to the length of the sequence. In further another embodiment, the specific length per seed is chosen according to a prior final template sequence.

For example, when K is 4, a seed table of a sequence is built as follows.

The sequence is divided into a plurality of seeds from the first base by per seed 4 mers, wherein the plurality of seeds therefrom is called a shift-0 seed set, and the content and a position of each seed are recorded.

Next, the sequence is divided into a plurality of seeds from the second base by per seed 4 mers, wherein the plurality of seeds therefrom is called a shift-1 seed set, and the content and a position of each seed are recorded.

Then, the sequence is divided into a plurality of seeds from the third base by per seed 4 mers, wherein the plurality of seeds therefrom is called a shift-2 seed set, and a content and a position of each seed are recorded.

After that, the sequence is divided into a plurality of seeds from the forth base by per seed 4 mers, wherein the plurality of seeds therefrom is called a shift-3 seed set, and the content and a position of each seed are recorded.

Finally, according to each seed set and the seeds therein mentioned above, a seed table with 4 mer length (4-mer seed table) is built. Note that a seed table with other seed length of the sequence may be built with a similar approach.

In addition, it is noted that the seed tables with different seed lengths (from the longest seed length need to the shortest seed length (2 mers)) of a sequence may be built at the same time. Or only a seed table with a specific length of a sequence may be built and the rest of the seed tables with other seed lengths may be built when needed.

The conditional ordering schedule for comparing the specific seed length tables of the reading sequences in the invention is to first compare the longest seed length tables of the reading sequences, and continue comparisons to the shortest seed length tables of the reading sequences.

Figure 2B:
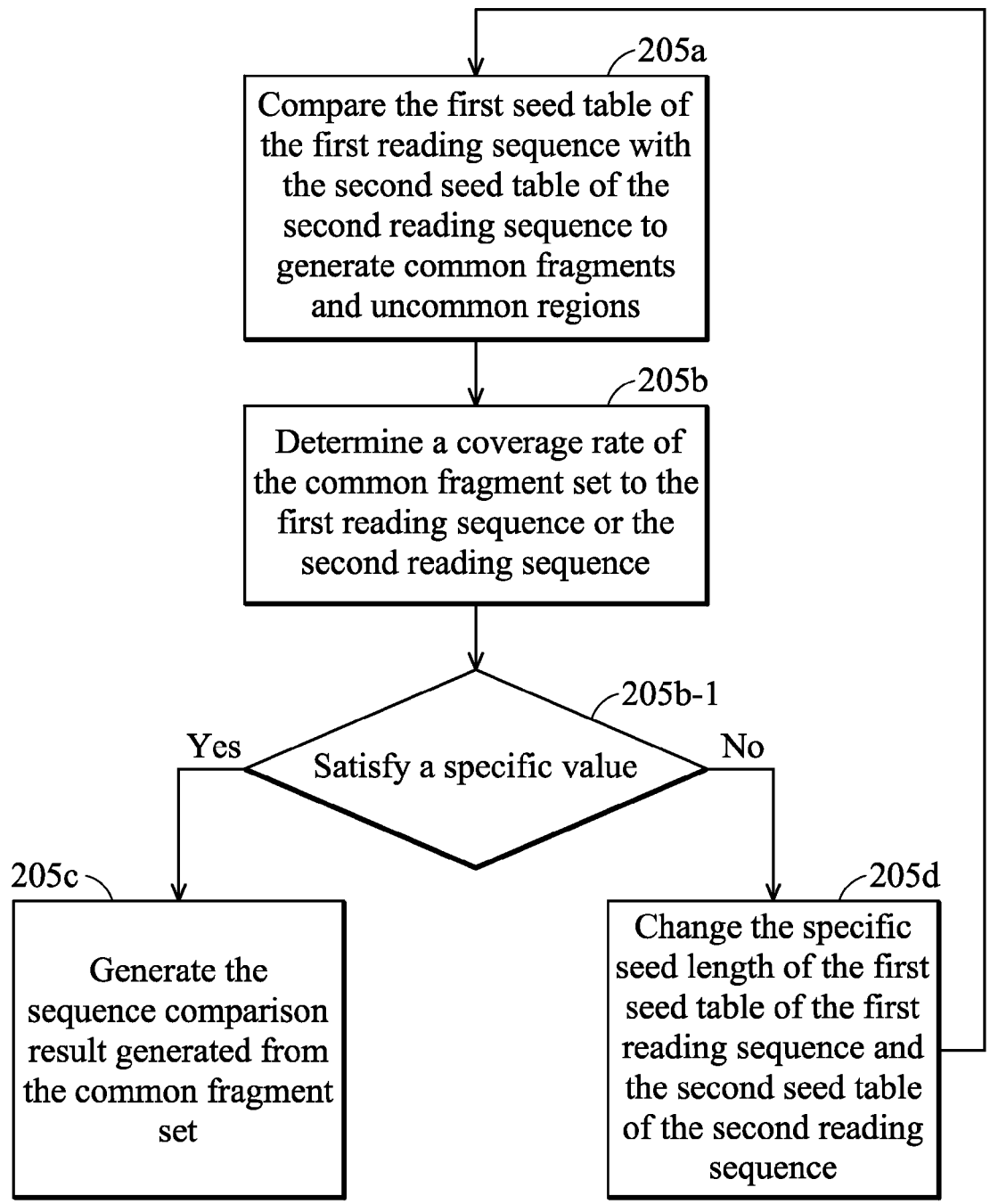

In one embodiment, see FIG. 2b, when the processor 103 compares the first reading sequence with the second reading sequence according to the comparison condition to generate a sequence comparison result (step 205), the processor 103 may compare the first seed table of the first reading sequence with the second seed table of the second reading sequence to generate common fragments and uncommon regions (step 205a). One common fragment consists of at least one common seed and is between two uncommon regions without interruption, and the longer the common fragment is, the greater the amount of the common seed contained therein is. All common fragments generated by comparing the first seed table with the second seed table form a common fragment set. The common seed is defined as the seed of the first reading sequence and the seed of the second reading sequence, when the content of a seed of the first reading sequence and a seed of the second reading sequence at a corresponding region or a region close to the corresponding region are equivalent. After comparing the first seed table of the first reading sequence with the second seed table of the second reading sequence to generate common fragments and uncommon regions (step 205a), the processor 103 then determines a coverage rate of the common fragment set to the first reading sequence or the second reading sequence (step 205 b). After that, when the value of the coverage rate satisfies a predetermined value, the processor 103 generates the sequence comparison result from the common fragment set (step 205 c). The value of the predetermined value is not limited, and may be 80-95%, or preferably 95%.

Comparatively, when the value of the coverage rate does not satisfy a predetermined value, the processor 103 changes the specific length of the first seeds constituting the first seed table of the first reading sequence and the specific length of the second seeds constituting the second seed table of the second reading sequence (i.e. changing the seed table of the first reading sequence with the specific seed length used in the comparison to the other seed table of the first reading sequence with the other specific seed and changing the seed table of the second reading sequence with the specific seed length used in the comparison to the other seed table of the second reading sequence with the other specific seed)) (step 205d). Next, the processor 103 compares the first seed table constituted by the first seeds with the changed specific length with the second seed table constituted by the second seeds with the changed specific length at the uncommon regions (step 205a) to generate second common fragments and second uncommon regions, wherein the second common fragments and the first common fragment set constitute a second common fragment set, determines a coverage rate of the second common fragment set to the first reading sequence or the second reading sequence (step 205b) and generates the sequence comparison result generated by the second common fragment set (step 205c) when the value of the coverage rate satisfies a predetermined value.

Or in other words, when the value of the coverage rate does not satisfy a predetermined value, the processor 103 changes the first seed table of the first reading sequence and the second seed table of the second reading sequence (i.e. continuing to perform comparisons of the specific seed length tables of the reading sequences according the conditional ordering schedule, until a value of the coverage rate of the specific seed length tables of the reading sequences does satisfy the predetermined value.) (repeating steps 205a, 205b and 205d) until the value of the coverage rate satisfies the predetermined value, and then generates the sequence comparison result generated by the second common fragment set (step 205c)

Figure 2C:
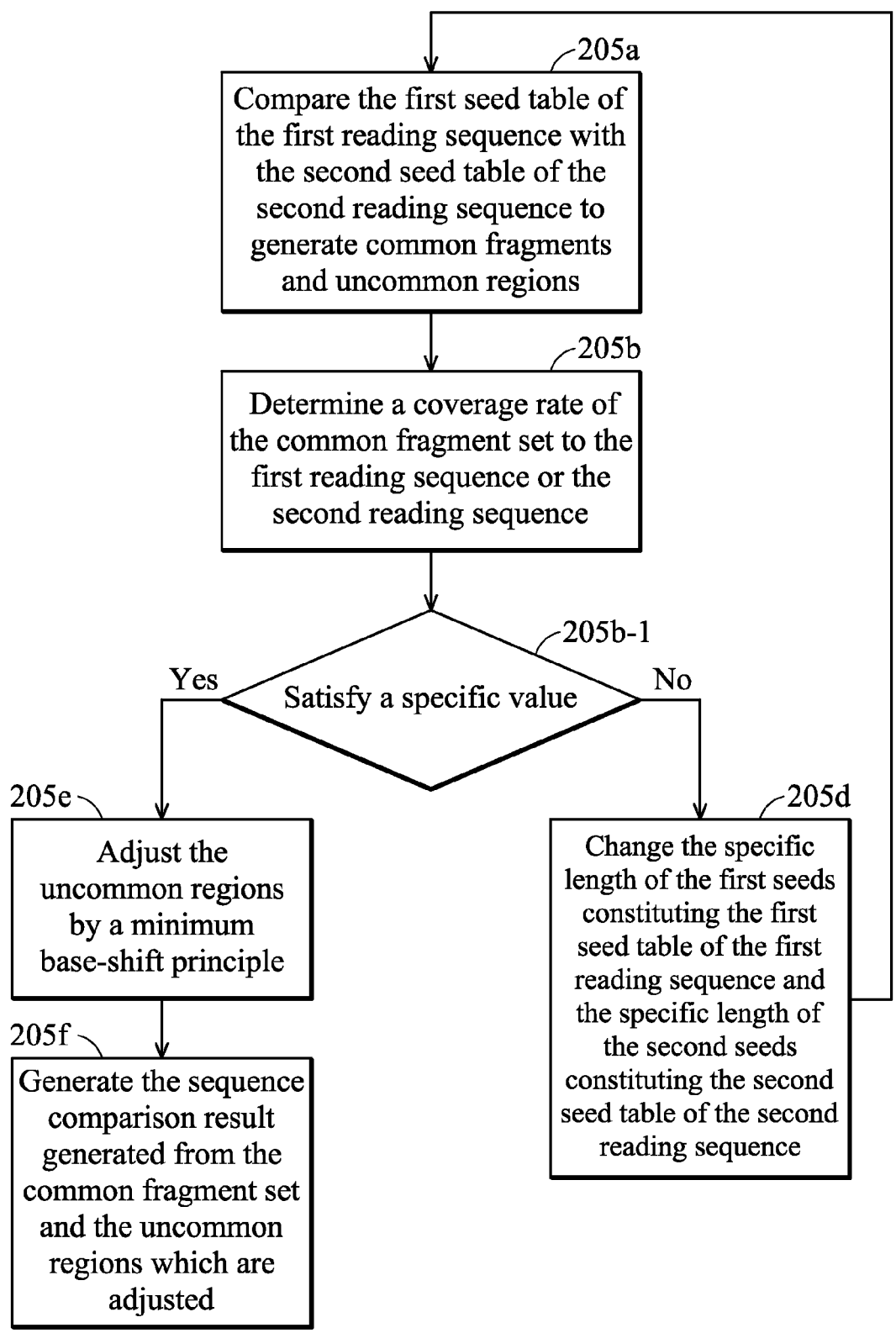
FIG. 2c shows a simplified flow chart of one embodiment of step 205 of the sequence compression method for two reading sequences.

In another embodiment, see FIG. 2c, after determining a coverage rate of the common fragment set to the first reading sequence or the second reading sequence (step 205b), when the value of the coverage rate satisfies a predetermined value, the processor 103 adjusts the uncommon regions by the minimum base-shift principle (205e) and generates the sequence comparison result from the adjusted common fragment set and the uncommon regions (205f). The value of the predetermined value is not limited, and may be 80-95%, or preferably 95%.

The minimum base-shift principle may comprise the following procedures.

First, each uncommon region is divided into shorter seed sets, and the alignment position of each base of a first reading sequence and the second reading sequence of each shorter seed set is shifted, so that, when compared, the greatest amount of bases of the first reading sequence and the second reading sequence is equivalently aligned, wherein there is at least one alignment manner for each shorter seed set. Second, a positive score is given for each of the equivalently aligned bases of each shorter seed set and a negative score or no score is given for each of the non-equivalently aligned bases of each shorter seed set. Then, a total score for each shorter seed set of the uncommon region is calculated and the alignment manner of the shorter seed set of the uncommon region with the highest score is selected.

Furthermore, one of the conditions for adjusting the uncommon regions by the minimum base-shift principle may be, to make no adjustment, when a length of an uncommon region for the first reading sequence is different from the second reading. In another condition, adjusting the uncommon regions is performed in all cases. When adjusting the uncommon regions by the minimum base-shift principle, seeds may be used from long seed length (shorter than the specific length) to short seed length (shorter than the specific length), or when adjusting the uncommon regions by the minimum base-shift principle, short seeds (shorter than the specific length) may be used for locally optimum solution.

Comparatively, when the value of the coverage rate does not satisfy a predetermined value, the processor 103 changes the specific length of the first seeds constituting the first seed table of the first reading sequence and the specific length of the second seeds constituting the second seed table of the second reading sequence (i.e. changing the seed table of the first reading sequence with the specific seed length used in the comparison to the other seed table of the first reading sequence with the other specific seed and changing the seed table of the second reading sequence with the specific seed length used in the comparison to the other seed table of the second reading sequence with the other specific seed) (step 205*d*). Next, the processor 103 compares the first seed table constituted by the first seeds with the changed specific length with the second seed table constituted by the second seeds with the changed specific length at the uncommon regions (step 205*a*) to generate second common fragments and second uncommon regions, wherein the second common fragments and the first common fragment set constitute a second common fragment set. Subsequently, the processor 103 determines a coverage rate of the second common fragment set to the first reading sequence or the second reading sequence (step 205*b*). Then the processor 103 adjusts the uncommon regions by the minimum base-shift principle when the value of the coverage rate satisfies the predetermined value (205*e*) and generates the sequence comparison result generated by the second common fragment set and the uncommon regions which are adjusted (205*f*).

Or in other words, when the value of the coverage rate does not satisfy a predetermined value, the processor 103 changes of the first seed table of the first reading sequence and the second seed table of the second reading sequence (i.e. continuing to perform comparisons of the specific seed length tables of the reading sequences according the conditional ordering schedule, until a value of the coverage rate of the specific seed length tables of the reading sequences does satisfy the predetermined value.) (repeating steps 205*a*, 250*b* and 205*d*) until the coverage rate satisfies the predetermined value, and then adjusts the uncommon regions by the minimum base-shift principle when the value of the coverage rate satisfies the predetermined value (205*e*). The processor 103 generates the sequence comparison result generated by the second common fragment set and the uncommon regions which are adjusted (205*f*). Then, the processor 103 outputs a final template sequence according to the sequence comparison result (step 207).

The first reading sequence and the second reading sequence may be read from a single sequence. In one embodiment, the single sequence is a concatenate sequence. The concatenate sequence may be read from a circle sequence, which has a known sequence part, such as a primer, and an unknown sequence part. The concatenate sequence may have primer-DNA repeat patterns. When the first reading sequence and the second reading sequence are read from a concatenate sequence having primer-DNA (DNA segment with connected primer) repeat patterns, first, the position and boundary of the primer of the concatenate are located. Second the position and boundary of the DNA are located, or "primer-DNA" pattern are located or "primer-DNA-primer" pattern are located. Then, the first reading sequence and the second reading sequence are obtained in the form of a "primer-DNA" pattern or "primer-DNA-primer" pattern.

More particularly, when the original sequence is a concatenate sequence having the primer-DNA (DNA segment with connected primer) repeat patterns, the seed tables of the primer and the seed tables sequence may be built first, and then the primer sequence is compared to possible positions in the concatenate sequences with the seed tables with longest seeds to locate the exact positions of the primers for retrieving the DNA segments. After that, the sequences of the DNA segments are obtained.

The sequence compression method for a plurality of sequences is detailed in the following, in another aspect of the invention.

Referring to FIG. 1 and FIG. 3, FIG. 1 shows a diagram of one embodiment of a sequence compression device of the invention and FIG. 3 shows a simplified flow chart of one embodiment of the sequence compression method performed by the device. The sequence compression device 100 may comprises a receiving unit 101 and a processor 103. First, the receiving unit 101 obtains a plurality of reading sequences from an identical source by a receiving unit (step 301). Next, the processor 103 selects one of the plurality of reading sequences as an initial template sequence (step 303). After the initial template sequence is selected, the processor 103 sets a comparison condition (step 305). The method to select the initial template sequence from the plurality of reading sequences may comprise: (i) selecting the longest reading sequence among the plurality of reading sequences as the initial template sequence; (ii) selecting the reading sequence having a length which is closest to the average length of the plurality of reading sequences as the initial template sequence; (iii) selecting the reading sequence having a length which has the highest number of occurrence, among the plurality of reading sequences as the initial template sequence; or (iv) randomly selecting the reading sequence among the input sequences as the initial template sequence.

Figure 4:
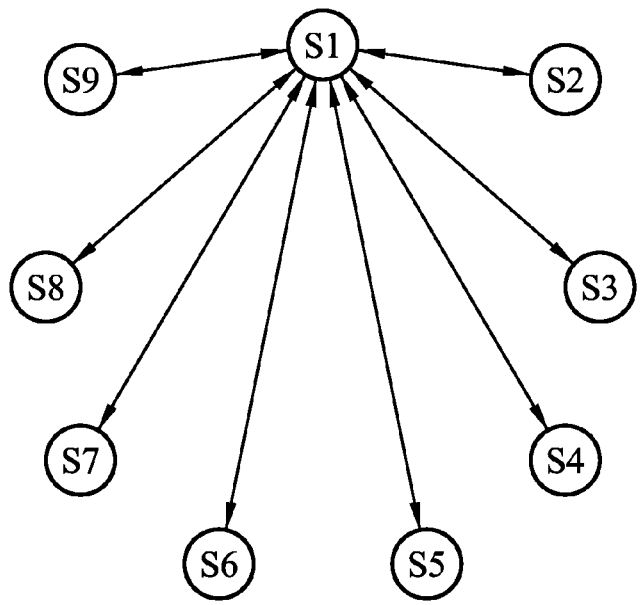
FIG. 4 shows a comparison method for the plurality of sequences of the invention.

After the initial template sequence is selected, the processor 103 compares the initial template sequence to each of the other sequences according to the comparison condition, to respectively generate comparison results (step 307). The comparison method for the plurality of sequences mentioned above is illustrated as FIG. 4. S1 to S9 represent different reading sequences, wherein S1 is selected as an initial template sequence.

Then, the processor 103 generates a sequence comparison result according to all respectively generated comparison results (step 309). Next, the processor 103 outputs a final template sequence according to the sequence comparison result (step 311). In another embodiment, the final template sequence may be updated during the comparison process. The final template sequence may be stored in the memory 105. The processor 103 compares the final template sequence to each of the plurality of reading sequences in order to generate a respective difference between the final template sequence and each of the plurality of reading sequences (step 313). In the embodiment that the final template sequence is updated during the comparison, the processor 103 compares all the versions of the final template sequence to each of the plurality of reading sequences to generate a respective difference of the plurality of reading sequences process corresponding to different versions of the final template sequence. The respective difference may include starting positions, lengths, ending positions, and contents. Finally, the processor 103 compresses the plurality of reading sequences according to the final template sequences and all generated differences between the final template sequence and the plurality of reading sequences in order to generate a compression file (step 315). The compression file may have a file format comprising a file header, the final template sequence, and a comparison difference of positions and contents corresponding to all generated differences between the final template sequence and the plurality of reading sequences.

The processor 103 may set the comparison condition according to a first seed table of the initial template sequence and second seed tables for reading sequences which are not selected. The first seed table of the initial template sequence may comprise a plurality of first seeds with a specific length constituting a plurality of first seed sets with different seeding start sites and the second seed table of the reading sequence which is not selected may comprise a plurality of second seeds with a specific length constituting a plurality of second seed sets with different seeding start sites, wherein the specific length of the first seeds of the first seed table and the specific length of the second seeds of the second seed table are of the same specific length.

A seed table of a sequence may be built by the processor 103. Definitions for a seed, a seed set and a seed table are the same as mentioned above. The approach for building a seed table is also the same as mentioned above.

In addition, it is noted that the seed tables with different seed lengths (from the longest seed length need to the shortest seed length (2 mers)) of a sequence may be built at the same time. Or only a seed table with a specific length of a sequence may be built and the rest of the seed tables with other seed lengths may be built when needed. Moreover, the seed tables of two sequences which are to be compared are built first and the rest of the seed tables may be built when needed.

Figure 3A:
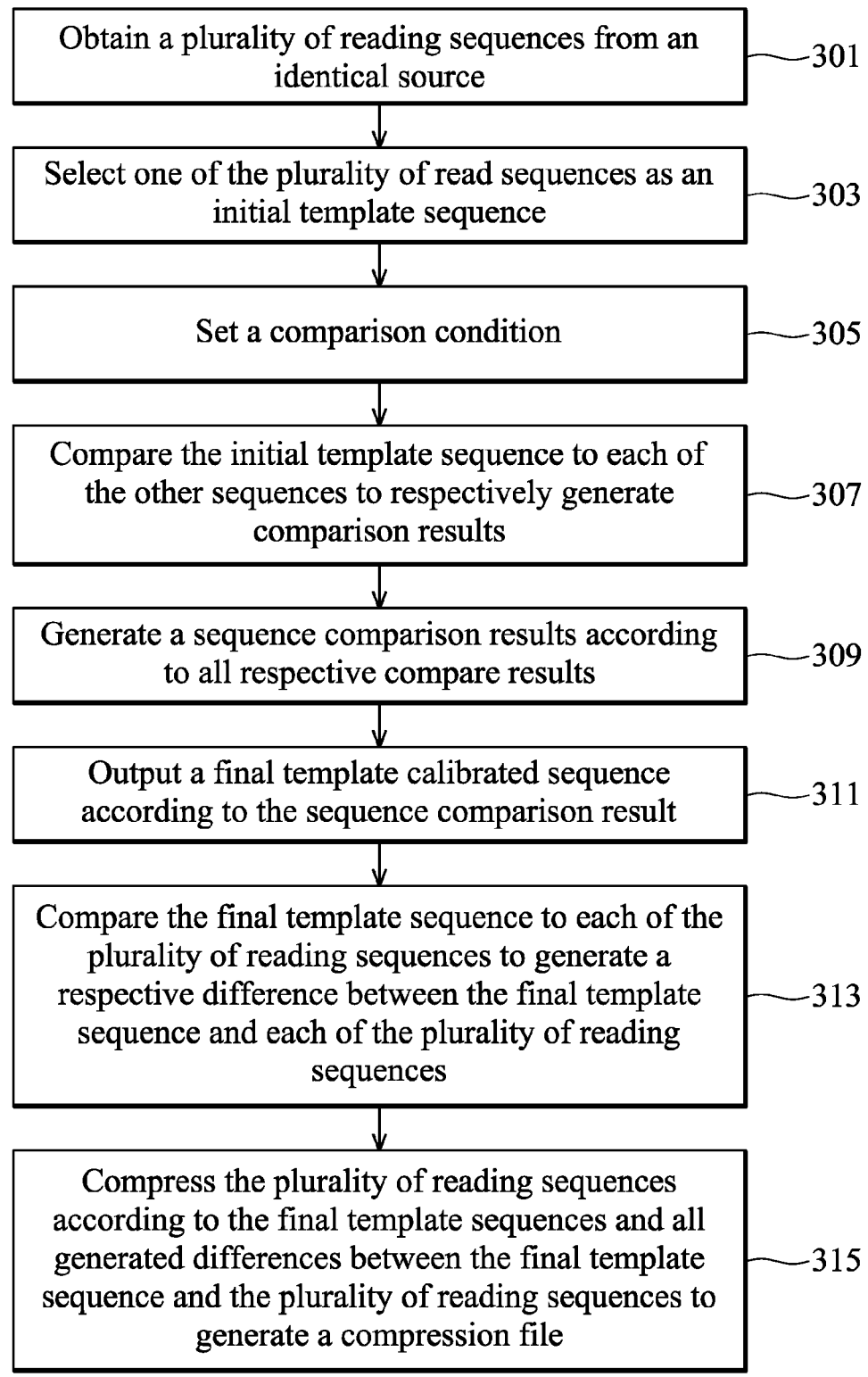
FIG. 3a shows a simplified flow chart of another embodiment of the sequence compression method for a plurality of reading sequences.
Figure 3B:
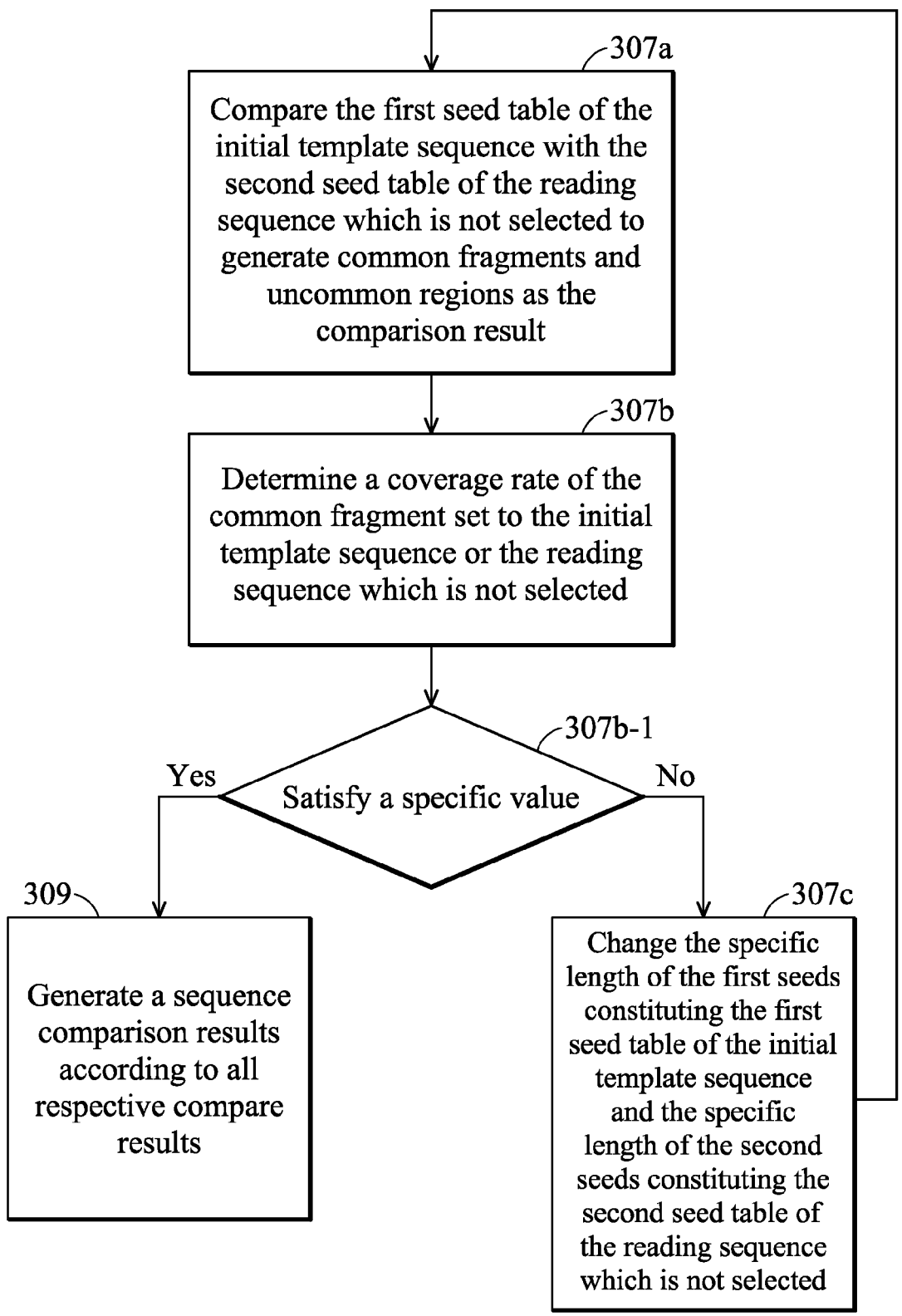

In one embodiment, see FIG. 3b, when the processor 103 compares the initial template sequence with the each of the other sequences according to the comparison condition, to respectively generate comparison results (step 307), in comparing the initial template sequence with one reading sequence which is not selected, the processor 103 may compare the first seed table of the initial template sequence with the second seed table of the reading sequence which is not selected to generate common fragments and uncommon regions as the comparison result (step 307a). One common fragment consists of at least one common seed and is between two uncommon regions without interruption, and the longer the common fragment is, the greater the amount of the common seed contained therein is. All common fragments generated by comparing the first seed table with the second seed table form a common fragment set. The common seed is defined as the seed of the initial template sequence and the seed of the reading sequence which is not selected, when the content of a seed of the initial template sequence and a seed of the reading sequence which is not selected at a corresponding region or a region close to the corresponding region are equivalent. After comparing the first seed table with the second seed table to generate common fragments and uncommon regions as the comparison result (step 307a), the processor 103 determines a coverage rate of the common fragment set to the initial template sequence or the reading sequence which is not selected (step 307b). When the value of the coverage rate satisfies a predetermined value, the processor 103 uses the common fragments to generating sequence comparison results according to all respectively generated comparison results (step 309). The value of the predetermined value is not limited, and may be 80-95%, or preferably 95%.

Comparatively, when the value of the coverage rate does not satisfy a predetermined value, the processor 103 changes the specific length of the first seeds constituting the first seed table of the initial template sequence and the specific length of the second seeds constituting the second seed table of the reading sequence which is not selected (i.e. continuing to perform comparisons of the specific seed length tables of the reading sequences according the conditional ordering schedule, until a value of the coverage rate of the specific seed length tables of the reading sequences does satisfy the predetermined value.) (step 307c). Next, the processor 103 compares the first seed table constituted by the first seeds with the changed specific length with the second seed table constituted by the second seeds with the changed specific length at the uncommon regions (step 307a) to generate a second common fragments and second uncommon regions, wherein the second common fragments and the first common fragment set constitute a second common fragment set, determines a coverage rate of the second common fragment set to the initial template sequence or the reading sequence which is not selected (step 307b) and uses the second common fragments to generate sequence comparison results according to all respectively generated comparison results (step 309) when the value of the coverage rate satisfies a predetermined value.

Or in other words, when the value of the coverage rate does not satisfy a predetermined value, the processor 103 changes the first seed table of the initial template sequence and the second seed table of the reading sequence which is not selected (i.e. continuing to perform comparisons of the specific seed length tables of the reading sequences according the conditional ordering schedule, until a value of the coverage rate of the specific seed length tables of the reading sequences does satisfy the predetermined value.) (repeating steps 307a, 307b and 307c) until the coverage rate satisfies the predetermined value, and then uses the second common fragments to generate a sequence comparison results according to all respectively generated comparison results (step 309).

Figure 3C:
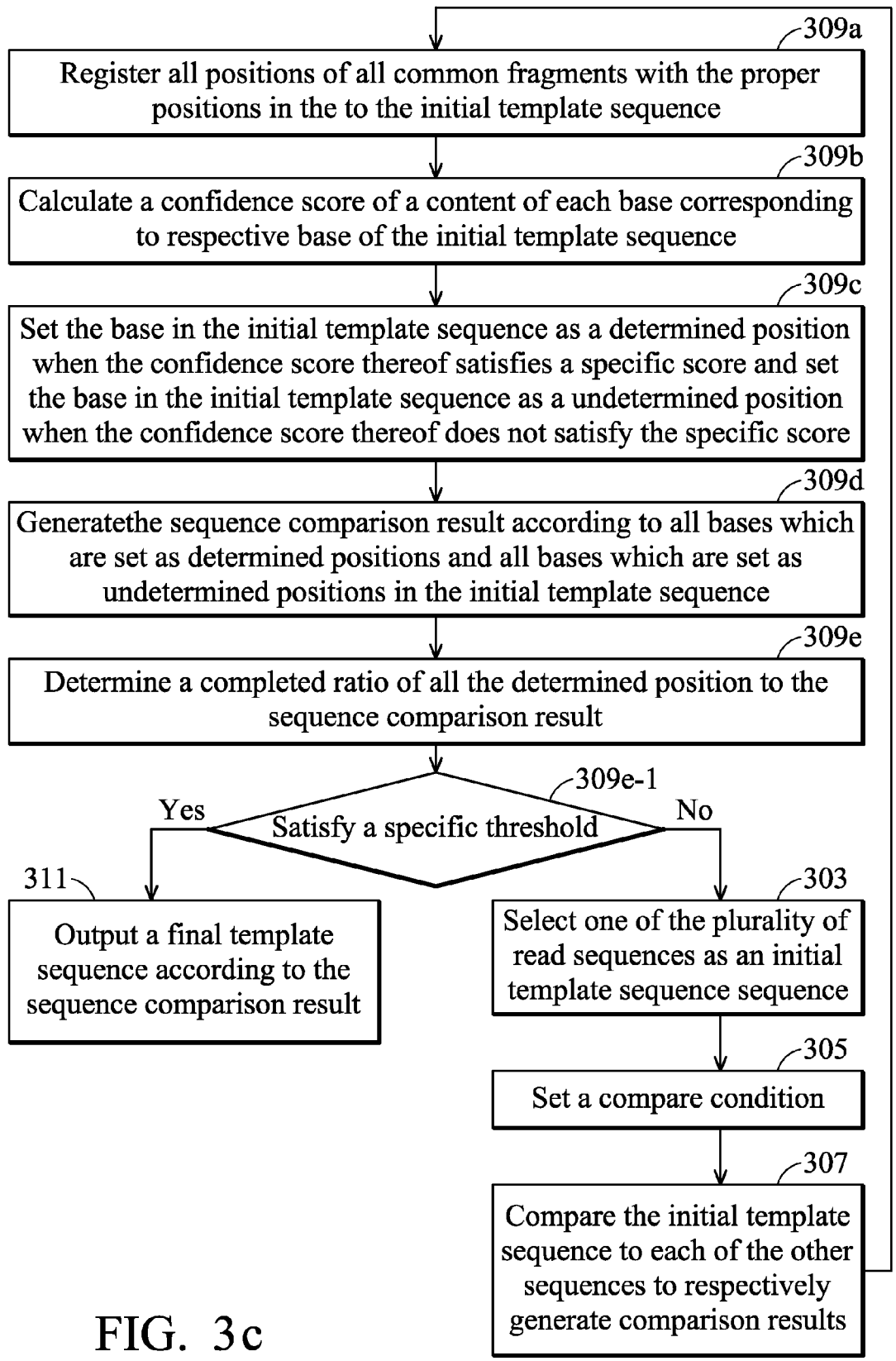
Figure 3D:
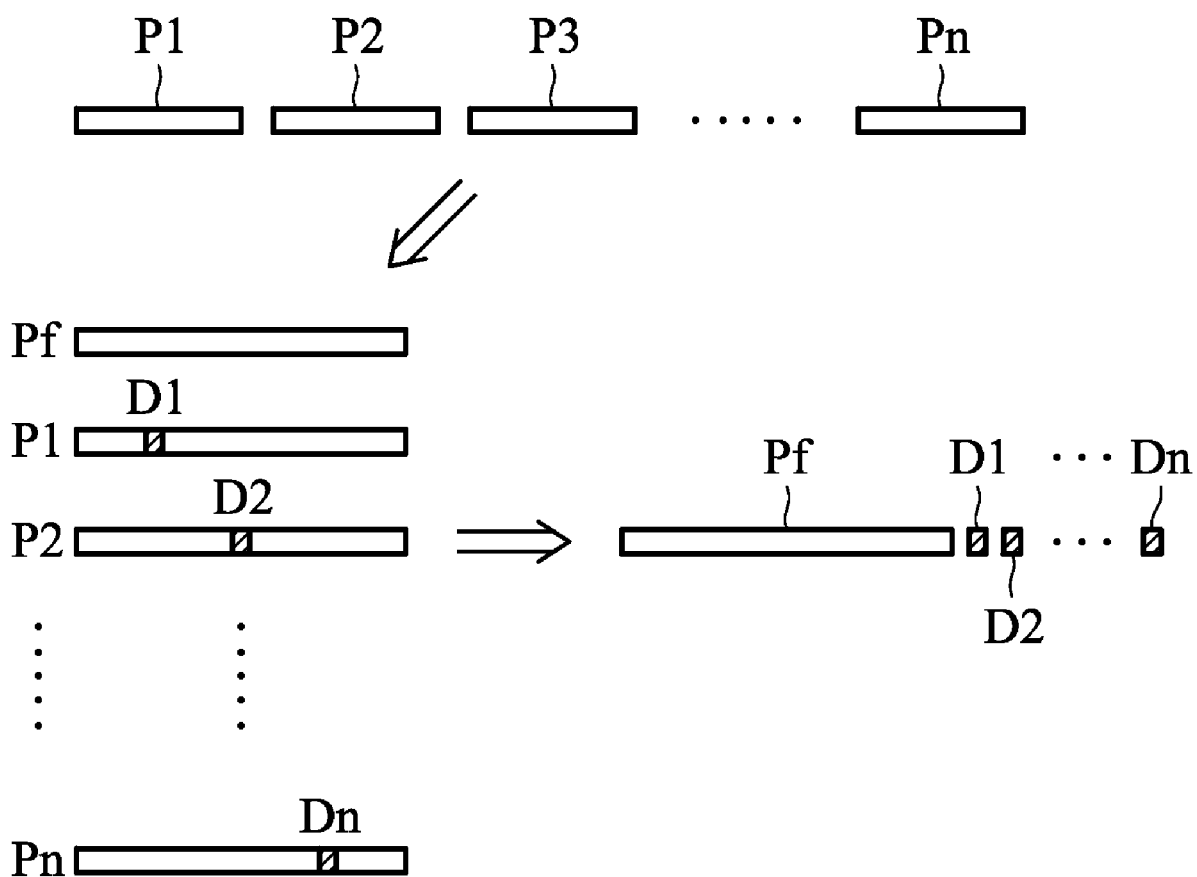
FIG. 3d shows a compression method for the plurality of sequences.

Procedures for generating sequence comparison results according to all respectively generated comparison results (step 309) may comprise the following (see FIG. 3c).

First, the processor 103 registers all positions of all common fragments obtained from generating sequence comparison results according to all respectively generated comparison results (step 307) with the proper positions in the initial template sequence (step 309a). Then, the processor 103 calculates a confidence score of a content of each base corresponding to the respective bases of the initial template sequence according to all common fragments (step 309b). Next, the processor 103 sets the base in the initial template sequence as a determined position when the confidence score thereof satisfies a specific score and sets the base in the initial template sequence as a undetermined position when the confidence score thereof does not satisfy a specific score (step 309c).

Figure 5:
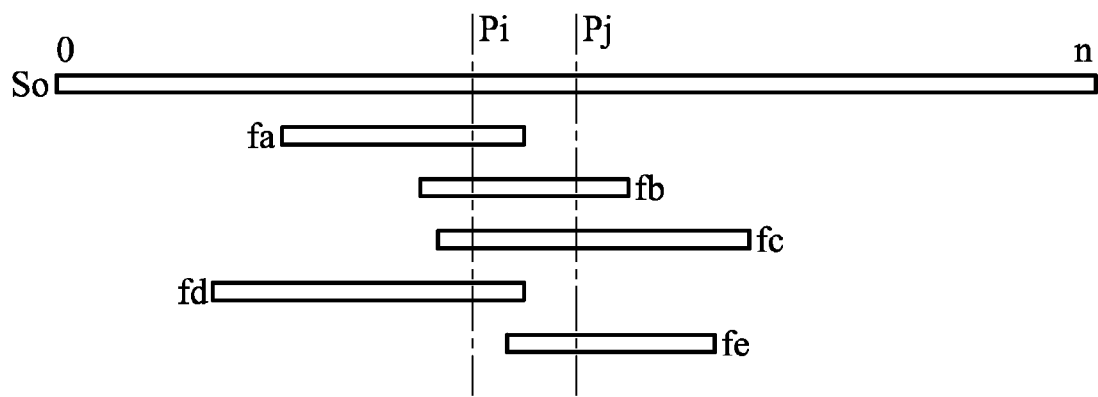
FIG. 5 shows an illustration for calculating a confidence score of a content of each position.

An illustration for calculating a confidence score of a content of each position is shown in FIG. 5

Pi and Pj are two positions corresponding to the template. fa-fe are common fragments generated from comparing two sequences. The confidence scores of fa-fe are a-e, respectively. The confidence score of each position is represented by $$C_P = \sum_X fx.$$

The confidence scores of contents of Pi and Pj are represented by $C_{pi}=(a+b+c+d)$ and $C_{pj}=(b+c+e)$, respectively.

After, the processor 103 generates the sequence comparison result according to all bases which are set as determined positions and all bases which are set as undetermined positions in the initial template sequence (step 309d). Subsequently, the processor 103 determines a completed ratio for all of the determined positions to the sequence comparison result (step 309e). Next, when the completed ratio satisfies a specific threshold, the processor 103 uses the sequence comparison result to output a final template sequence according to the sequence comparison result (step 311). The value of the specific threshold is not limited, and may be 80-95%, or preferably 95%.

Comparatively, when the completed ratio does not satisfy a predetermined value, the processor 103 repeats the steps 303, 305 and 307, wherein a new template sequence is selected from the plurality of reading sequences without the first template and the first template is stopped from being compared, and wherein new common fragments and new uncommon regions are generated from comparing the new template sequence with the other reading sequences. After that, the processor 103 registers all positions of all new common fragments with the proper positions in the sequence comparison result (step 309a), calculates a confidence score of a content of each undetermined positions corresponding to the sequence comparison result according to the new common fragments which correspond to the positions of the undetermined positions (step 309b). Then, the processor 103 sets each base of the undetermined positions in the sequence comparison result as a new determined position when the confidence score thereof satisfies a specific score and still set the base in the undetermined positions as a undetermined position when the confidence score thereof does not satisfy a specific score (step 309c) and generates a new sequence comparison result by the sequence comparison result and the new determined positions (step 309d). Next, the processor 103 determines a completed ratio of all the determined positions to the new sequence comparison result. When the completed ratio satisfies the specific threshold, the new sequence comparison result is used to output a final template sequence (step 311). The processor 103 outputs a final template sequence according to new sequence comparison result.

Furthermore, in still other embodiment, the processor 103 may adjust the undetermined positions of the sequence comparison result by a minimum base-shift principle before outputting a final template sequence (step 311). The procedures and conditions for the minimum base-shift principle are the same as that mentioned above.

The compression method for the plurality of sequences mentioned above is illustrated as FIG. 3d. Labels P1-Pn represent the plurality of reading sequences. A final template sequence Pf is output according to the sequence comparison result. The processor 103 compares the final template sequence Pf with the reading sequences P1-Pn, and respectively generates differences D1-Dn between the final template sequence Pf and the reading sequences P1-Pn. Then, the processor 103 may compress the plurality of reading sequences just by way of storing the final template sequence Pf and all generated differences D1-Dn. The compression file may comprise the final template sequence Pf and all generated differences D1-Dn, not all reading sequences P1-Pn. Therefore, the compression method can save a lot of capacity of storage.

Figure 6:
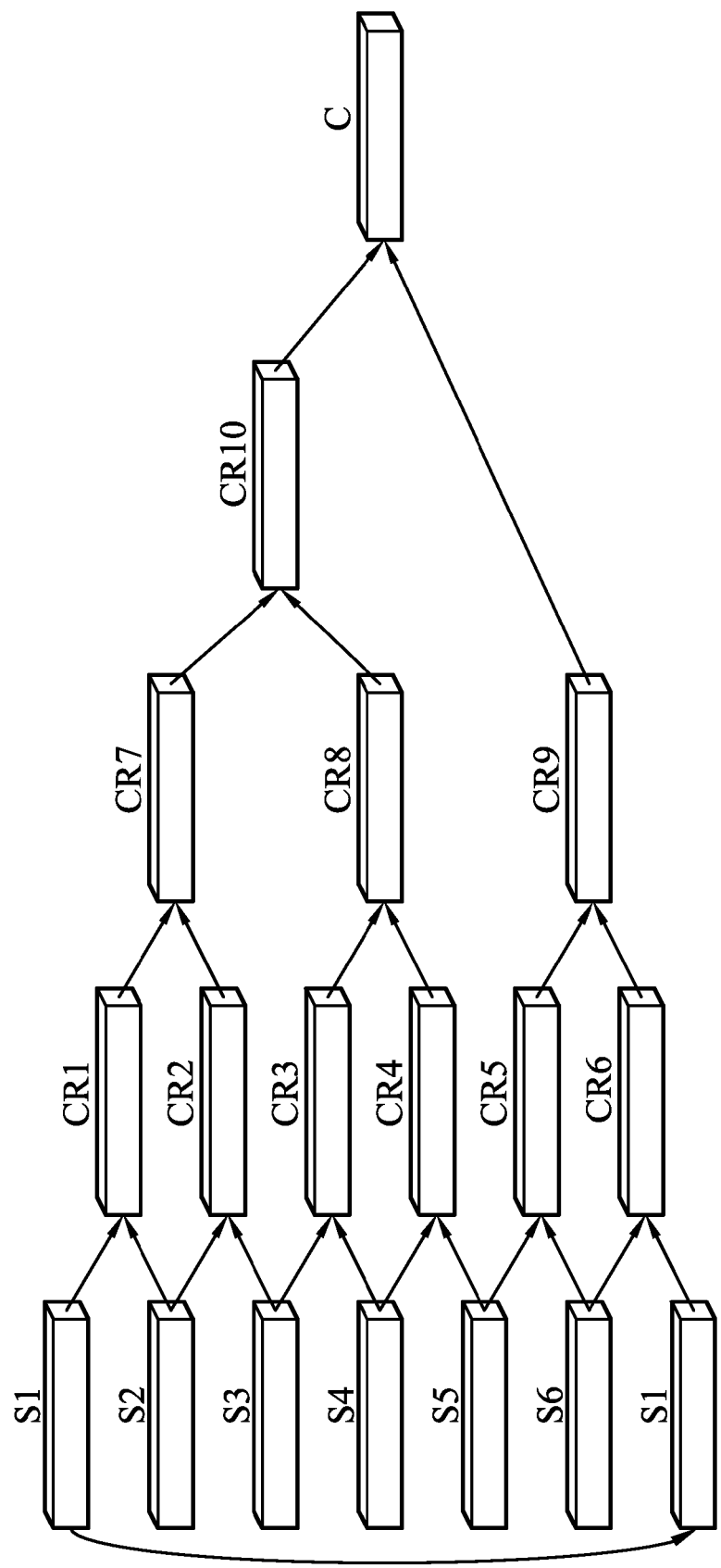
FIGS. 6-8 shows other comparison methods for the plurality of sequences of the invention.
Figure 7:
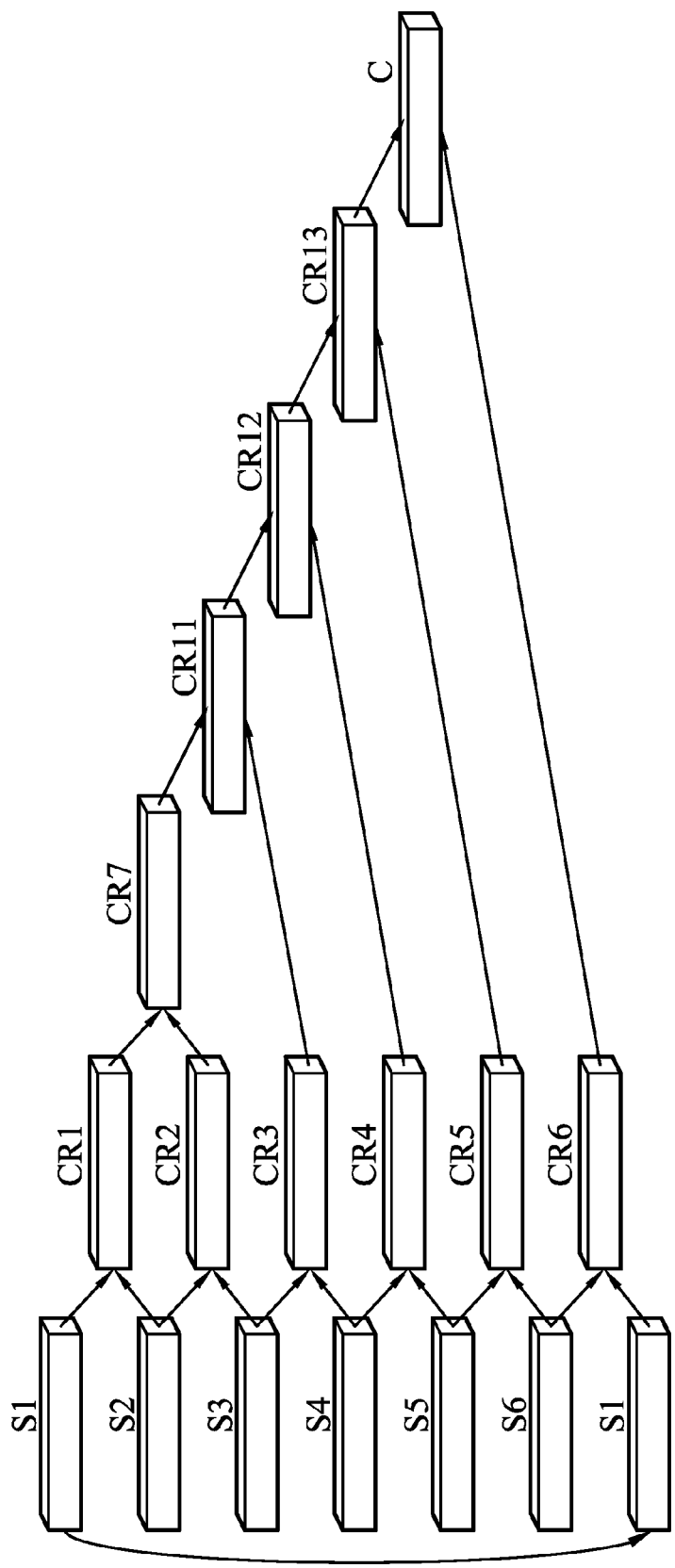
Figure 8:
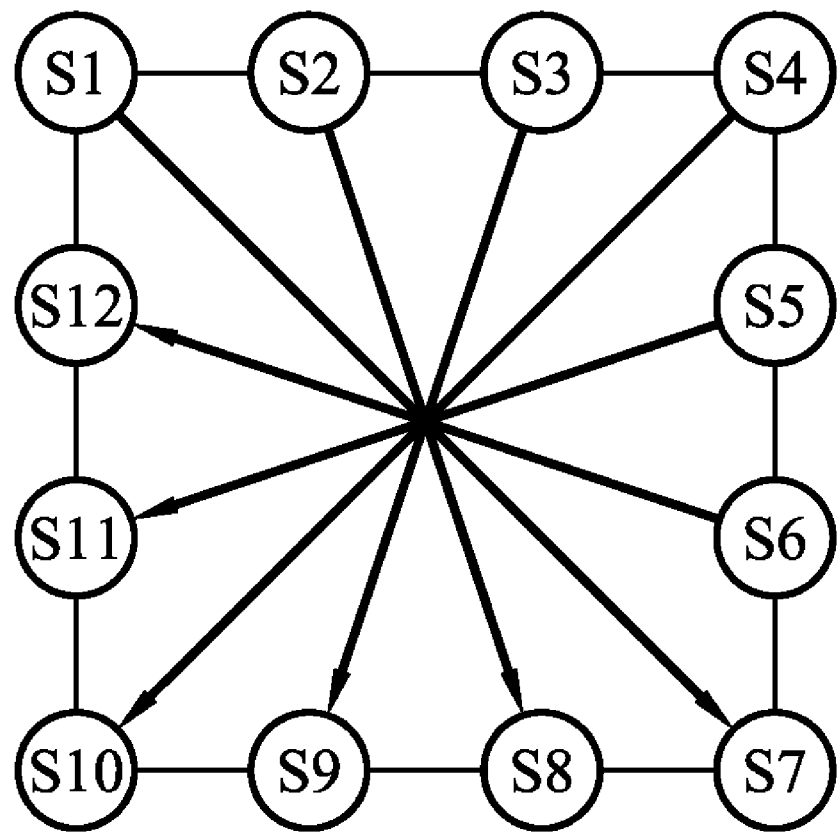

In still another aspect, there are other methods for comparison of the plurality of sequences in the sequence compression method of the invention. See FIGS. 6-8, wherein FIGS. 6-8 show different methods for comparing the plurality of sequences in the sequence compression method of the invention.

S1 to S12 represent different reading sequences. CR1 to CR13 represent different sequence comparison results generated from different comparison orders. C represents an outputted final template sequence.

Moreover, the plurality of reading sequences may be read from a single sequence. In one embodiment, the single sequence is a concatenate sequence. The concatenate sequence may be read from a circle sequence, which has a known sequence part, such as a primer, and an unknown sequence part. The concatenate sequence may have primer-DNA repeat patterns. The method to retrieve DNA fragments is similar to that which was mentioned above.

What is claimed is:

1. A data compression method, comprising:
   (a) obtaining a first reading sequence and a second reading sequence from an identical source by a receiving unit;
   (b) comparing the first reading sequence with the second reading sequence according to a comparison condition to generate a sequence comparison result by a processor; and
   (c) outputting a final template sequence according to the sequence comparison result by the processor,
   (d) comparing the final template sequence to each of the first and second reading sequences, to generate a respective difference between the final template sequence and each of the first and second reading sequences by the processor; and
   (e) compressing the first and second reading sequences according to the final template sequences and all generated differences between the final template sequence and the first and second reading sequences, to generate a compression file by the processor,
   wherein the comparison condition is set according to a first seed table of the first reading sequence comprising a plurality of first seeds with a specific length constituting a plurality of first seed sets with different seeding start sites and a second seed table of the second reading sequence comprising a plurality of second seeds with a specific length constituting a plurality of second seed sets with different seeding start sites, and wherein the specific length of the first seeds of the first seed table and the specific length of the second seeds of the second seed table are of the same specific length.

2. The data compression method as claimed in claim 1, wherein the first reading sequence and the second reading sequence are from a single sequence.

3. The data compression method as claimed in claim 2, wherein the single sequence is a concatenate sequence.

4. The data compression method as claimed in claim 3, wherein the concatenate sequence has primer-DNA repeat patterns.

5. The data compression method as claimed in claim 1, wherein the specific length of the first seeds or the second seeds is a positive integer of at least than 2.

6. The data compression method as claimed in claim 1, wherein the specific length of the first seeds or the second seeds is a positive integer having a value ranging from 3 to 9.

7. The data compression method as claimed in claim 1, wherein a basis for choosing the specific length of the first seeds or the second seeds may comprise experiences of a user, the length of the sequence or the accuracy of a prior final template sequence from data compression method.

8. The data compression method as claimed in claim 1, wherein the step (b) comprises:
   comparing the first seed table with the second seed table to generate common fragments and uncommon regions, wherein one common fragment consists of at least one common seed and is between two uncommon regions without interruption, and the longer the common fragment is, the greater the amount of the common seed contained therein is, and wherein all common fragments generated by comparing the first seed table with the second seed table form a common fragment set;

determining a coverage rate of the common fragment set to the first reading sequence or the second reading sequence; and generating the sequence comparison result from the common fragment set when the value of the coverage rate satisfies a predetermined value.

9. The data compression method as claimed in claim 8 wherein, when the value of the coverage rate does not satisfy the predetermined value, the method further comprising:

changing the specific length of the first seeds constituting the first seed table of the first reading sequence and the specific length of the second seeds constituting the second seed table of the second reading sequence;

comparing the first seed table constituted by the first seeds with the changed specific length with the second seed table constituted by the second seeds with the changed specific length at the uncommon regions to generate a second common fragments and second uncommon regions, wherein the second common fragments and the first common fragment set constitute a second common fragment set;

determining a coverage rate of the second common fragment set to the first reading sequence or the second reading sequence; and generating the sequence comparison result generated by the second common fragment set when the value of the coverage rate satisfies the predetermined value.

10. The data compression method as claimed in claim 8, further comprising:

continually changing the specific length when the coverage rate does not satisfy the predetermined value until the coverage rate until the coverage rate satisfies the predetermined value.

11. The data compression method as claimed in claim 8, wherein the common seed is defined as the seed of the first reading sequence and the seed of the second reading sequence, when the content of a seed of the first reading sequence and a seed of the second reading sequence at a corresponding region or a region close to the corresponding region are equivalent.

12. The data compression method as claimed in claim 1, wherein the step (b) comprises:

comparing the first seed table with the second seed table to generate common fragments and uncommon regions, wherein one common fragment consists of at least one common seed and is between two uncommon regions without interruption, and the longer the common fragment is, the greater the amount of the common seed contained therein is, and wherein all common fragments generated by comparing the first seed table with the second seed table form a common fragment set;

determining a coverage rate of the common fragment set to the first reading sequence or the second reading sequence;

adjusting the uncommon regions by the minimum base-shift principle when the value of the coverage rate satisfies a predetermined value; and generating the sequence comparison result from the adjusted common fragment set and the uncommon regions.

13. The data compression method as claimed in claim 12, when the value of the coverage rate does not satisfy the predetermined value, further comprising:

changing the specific length of the first seeds constituting the first seed table of the first reading sequence and the specific length of the second seeds constituting the second seed table of the second reading sequence;

comparing the first seed table constituted by the first seeds with the changed specific length with the second seed table constituted by the second seeds with the changed specific length at the uncommon regions to generate a second common fragments and second uncommon regions, wherein the second common fragments and the first common fragment set constitute a second common fragment set;

determining a coverage rate of the second common fragment set to the first reading sequence or the second reading sequence; and adjusting the uncommon regions by the minimum base-shift principle when the value of the coverage rate satisfies the predetermined value; and generating the sequence comparison result from the adjusted common fragment set and the uncommon regions.

14. The data compression method as claimed in claim 12, further comprising:

continually changing the specific length of the first seeds constituting the first seed table of the first reading sequence and the specific length of the second seeds constituting the second seed table of the second reading sequence when the coverage rate does not satisfy the predetermined value until the coverage rate until the coverage rate satisfies the predetermined value.

15. The data compression method as claimed in claim 12, wherein the common seed is defined as the seed of the first reading sequence and the seed of the second reading sequence, when the content of a seed of the first reading sequence and a seed of the second reading sequence at a corresponding region or a region close to the corresponding region are equivalent.

16. The data compression method as claimed in claim 12, wherein the minimum base-shift principle comprises:

dividing each uncommon region into shorter seed sets, and shifting the alignment position of each base of a first reading sequence and the second reading sequence of each shorter seed set, so that, when compared, the greatest amount of bases of the first reading sequence and the second reading sequence is equivalently aligned, wherein there is at least one alignment manner for each shorter seed set;

giving a positive score for each of the equivalently aligned bases of each shorter seed set and giving a negative score for each of the non-equivalently aligned bases of each shorter seed set; and calculating a total score for each shorter seed set of the uncommon region, and selecting the alignment manner of the shorter seed set of the uncommon region with the highest score.

17. The data compression method as claimed in claim 1, wherein the respective difference between the final template sequence and each of the first and second reading sequences in step (d) comprises starting positions, lengths, and contents.

18. The data compression method as claimed in claim 1, wherein the respective difference between the final template sequence and each of the first and second reading sequences in step (d) comprises starting positions, ending positions, and contents.

19. The data compression method as claimed in claim 1, wherein the compression file in step (e) has a file format comprising a file header, the final template sequence, and a comparison difference of positions and contents corresponding to all generated differences between the final template sequence and the first and second reading sequences.

20. A data compression method, comprising:
(a) obtaining a plurality of reading sequences from an identical source by a receiving unit;
(b) selecting one of the plurality of reading sequences as an initial template sequence by a processor;
(c) comparing the initial template sequence to each of the other sequences according to a comparison condition, to respectively generate comparison results by the processor;
(d) generating a sequence comparison result according to all respectively generated comparison results by the processor; and
(e) outputting a final template sequence according to the sequence comparison result by the processor,
(f) comparing the final template sequence to each of the plurality of reading sequences, to generate a respective difference between the final template sequence and each of the plurality of reading sequences by the processor; and
(g) compressing the plurality of reading sequences according to the final template sequences and all generated differences between the final template sequence and the plurality of reading sequences, to generate a compression file by the processor,
wherein the comparison condition is set according to a first seed table of the initial template sequence comprising a plurality of first seeds with a specific length constituting a plurality of first seed sets with different seeding start sites and a second seed table of the reading sequence which is not selected comprising a plurality of second seeds with a specific length constituting a plurality of second seed sets with different seeding start sites, and wherein the specific length of the first seeds of the first seed table and the specific length of the second seeds of the second seed table are of the same specific length.

21. The data compression method as claimed in claim 20, wherein the plurality of reading sequences are from a single sequence.

22. The data compression method as claimed in claim 21, wherein the single sequence is a concatenate sequence.

23. The data compression method as claimed in claim 22, wherein the concatenate sequence has primer-DNA repeat patterns.

24. The data compression method as claimed in claim 20, wherein the specific length of the first seeds or the second seeds is a positive integer of at least 2.

25. The data compression method as claimed in claim 20, wherein the specific length of the first seeds or the second seeds is a positive integer of 3-9.

26. The data compression method as claimed in claim 20, wherein a basis for choosing the specific length of the first seeds or the second seeds may comprise experiences of a user, the length of the sequence or the accuracy of a prior final template sequence from data compression method.

27. The data compression method as claimed in claim 20, wherein comparing the initial template sequence with one reading sequence which is not selected in the step (c) comprises:
comparing the first seed table with the second seed table to generate common fragments and uncommon regions as the comparison result, wherein one common fragment consists of at least one common seed and is between two uncommon regions without interruption, and the longer the common fragment is, the greater the amount of the common seed contained therein is, and wherein all common fragments generated by comparing the first seed table with the second seed table form a common fragment set;
determining a coverage rate of the common fragment set to the initial template sequence or the reading sequence which is not selected; and
using the common fragments in the step (d) when the value of the coverage rate satisfies a predetermined value.

28. The data compression method as claimed in claim 27, further comprising: continually changing the specific length of the first seeds constituting the first seed table of the first reading sequence and the specific length of the second seeds constituting the second seed table of the second reading sequence when the coverage rate does not satisfy the predetermined value until the coverage rate until the coverage rate satisfies the predetermined value.

29. The data compression method as claimed in claim 27, wherein the step (d) further comprises:
registering all positions of all common fragments obtained from the step (c) with the proper positions in the initial template sequence; and
calculating a confidence score for the content of each base corresponding to respective template sequence bases according to all common fragments;
setting the base in the initial template sequence as a determined position when the confidence score for the content of each base corresponding to respective template sequence bases satisfies a specific score and setting the base in the initial template sequence as an undetermined position when the confidence score for the content of each base corresponding to respective template sequence bases does not satisfy a specific score;
generating the sequence comparison result according to all bases which are set as determined positions and all bases which are set as undetermined positions in the initial template sequence;
determining a completed ratio for all of the determined positions to the sequence comparison result; and
using the sequence comparison result in the step (e) when the completed ratio satisfies a specific threshold.

30. The data compression method as claimed in claim 29, when the value of the coverage rate does not satisfy the predetermined value, further comprising:
repeating the step (c), wherein a new template sequence is selected from the plurality of reading sequences without the first template and the first template is stopped from being compared, and wherein the new common fragments and the new uncommon regions are generated from comparing the new template sequence with the other reading sequences;
registering all positions of all new common fragments with the proper positions in the sequence comparison result; and
calculating a confidence score for the content of each undetermined positions corresponding to respective bases of the sequence comparison result according to the new common fragments which correspond to the positions of the undetermined positions;
setting each base of the undetermined positions in the sequence comparison result as a new determined position when the confidence score thereof satisfies a specific score, and still setting the base in the undetermined positions as a undetermined position when the confidence score thereof does not satisfy a specific score;
generating a new sequence comparison result according to the sequence comparison result and the new determined positions;

determining a completed ratio of all the determined positions to the new sequence comparison result; and using the new sequence comparison result in the step (e) when the completed ratio satisfies a specific threshold.

31. The data compression method as claimed in claim 29, further comprising adjusting the undetermined positions of the sequence comparison result by a minimum base-shift principle before the step (e).

32. The data compression method as claimed in claim 20, wherein the respective difference between the final template sequence and each of the plurality of reading sequences in step (f) comprises starting positions, lengths, and contents.

33. The data compression method as claimed in claim 20, wherein the respective difference between the final template sequence and each of the plurality of reading sequences in step (f) comprises starting positions, ending positions, and contents.

34. The data compression method as claimed in claim 20, wherein the compression file in step (g) has a file format comprising a file header, the final template sequence, and a comparison difference of positions and contents corresponding to all generated differences between the final template sequence and the plurality of reading sequences.

35. A sequence compression device, comprising:
a receiving unit for obtaining a plurality of reading sequences from an identical source; and
a processor for performing steps which comprise:
(a) selecting one of the plurality of reading sequences as an initial template sequence;
(b) comparing the initial template sequence to each of the other sequences according to a comparison condition, to respectively generate comparison results;
(c) generating a sequence comparison result according to all respectively generated comparison results;
(d) outputting a final template sequence according to the sequence comparison result,
(e) comparing the final template sequence to each of the plurality of reading sequences, to generate a respective difference between the final template sequence and each of the plurality of reading sequences by the processor; and
(f) compressing the plurality of reading sequences according to the final template sequences and all generated differences between the final template sequence and the plurality of reading sequences, to generate a compression file by the processor,
wherein the comparison condition is set according to a first seed table of the initial template sequence comprises a plurality of first seeds with a specific length constituting a plurality of first seed sets with different seeding start sites and a second seed table of the reading sequence which is not selected comprises a plurality of second seeds with a specific length constituting a plurality of second seed sets with different seeding start sites, and wherein the specific length of the first seeds of the first seed table and the specific length of the second seeds of the second seed table are of the same specific length.

36. The sequence compression device as claimed in claim 35, wherein the step (b) comprises:
comparing the first seed table with the second seed table to generate common fragments and uncommon regions as the comparison result, wherein one common fragment consists of at least one common seed and is between two uncommon regions without interruption, and the longer the common fragment is, the greater the amount of the common seed contained therein is;
determining a coverage rate of the common fragment set to the initial template sequence or the reading sequence which is not selected; and
using the common fragments in the step (d) when the value of the coverage rate satisfies a predetermined value.

* * * * *